(12) United States Patent
Taylor et al.

(10) Patent No.: US 8,205,620 B2
(45) Date of Patent: Jun. 26, 2012

(54) TWO PIECE ANVIL FOR SURGICAL STAPLER

(75) Inventors: Eric J. Taylor, Southington, CT (US); Peter Hathaway, Lebanon, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

(21) Appl. No.: 13/086,611

(22) Filed: Apr. 14, 2011

(65) Prior Publication Data

US 2011/0192880 A1    Aug. 11, 2011

Related U.S. Application Data

(62) Division of application No. 12/189,939, filed on Aug. 12, 2008, now Pat. No. 7,942,304.

(60) Provisional application No. 60/981,129, filed on Oct. 19, 2007.

(51) Int. Cl.
*B25C 5/02* (2006.01)
*A61B 17/068* (2006.01)

(52) U.S. Cl. ......... 128/898; 227/19; 227/175.1; 606/75; 606/139; 606/219

(58) Field of Classification Search ............... 227/19, 227/108, 154, 155, 175.1, 176.1, 178.1; 128/898; 606/219, 139, 75
See application file for complete search history.

(56) References Cited

U.S. PATENT DOCUMENTS

| | | |
|---|---|---|
| 3,160,890 A | 12/1964 | Roger |
| 3,490,675 A | 1/1970 | Green et al. |
| 3,499,591 A | 3/1970 | Green |
| 3,795,034 A | 3/1974 | Strekopytov et al. |
| 4,256,251 A | 3/1981 | Moshofsky |
| 4,305,539 A | 12/1981 | Korolkov et al. |
| 4,402,444 A | 9/1983 | Green |
| 4,493,322 A | 1/1985 | Becht |
| 4,506,670 A | 3/1985 | Crossley |
| 4,506,671 A | 3/1985 | Green |
| 4,525,489 A | 6/1985 | Narayan |
| 4,605,001 A | 8/1986 | Rothfuss et al. |
| 4,610,383 A | 9/1986 | Rothfuss et al. |
| 4,633,874 A | 1/1987 | Chow et al. |
| 4,648,542 A | 3/1987 | Fox et al. |
| 4,664,305 A | 5/1987 | Blake et al. |
| 4,691,853 A | 9/1987 | Storace |
| 4,715,520 A | 12/1987 | Roehr et al. |
| 4,747,531 A | 5/1988 | Brinkerhoff et al. |
| 4,848,637 A | 7/1989 | Pruitt |
| 4,887,756 A | 12/1989 | Puchy |
| 4,930,503 A | 6/1990 | Pruitt |
| 4,978,049 A | 12/1990 | Green |
| 5,100,041 A | 3/1992 | Storace |
| 5,180,092 A | 1/1993 | Crainich |
| 5,297,714 A | 3/1994 | Kramer |
| 5,413,268 A | 5/1995 | Green et al. |
| 5,456,400 A | 10/1995 | Shichman et al. |
| 5,465,896 A | 11/1995 | Allen et al. |
| 5,482,197 A | 1/1996 | Green et al. |
| 5,497,933 A | 3/1996 | DeFonzo et al. |
| 5,516,025 A | 5/1996 | Eriksson |
| 5,630,541 A | 5/1997 | Williamson, IV et al. |

(Continued)

*Primary Examiner* — Rinaldi Rada
*Assistant Examiner* — Gloria R Weeks

(57) ABSTRACT

A surgical stapling apparatus includes a stapling assembly including a staple cartridge for retaining and selectively releasing a plurality of staples, a forming member engageable by a staple during formation thereof, and first and second anvil sections for forming the staples. The first and second anvil sections are configured for independent actuation. A method of stapling first and second sections of tissue is also disclosed.

17 Claims, 8 Drawing Sheets

U.S. PATENT DOCUMENTS

| | | |
|---|---|---|
| 5,645,567 A | 7/1997 | Crainich |
| 5,829,662 A | 11/1998 | Allen et al. |
| 5,938,101 A | 8/1999 | Izuchukwu et al. |
| D480,808 S | 10/2003 | Wells et al. |
| 6,872,214 B2 | 3/2005 | Sonnenschein et al. |
| 6,923,360 B2 | 8/2005 | Sesek et al. |
| 6,981,627 B2 | 1/2006 | Tsai |
| 6,986,451 B1 | 1/2006 | Mastri et al. |
| 7,032,799 B2 | 4/2006 | Viola et al. |
| 7,044,353 B2 | 5/2006 | Mastri et al. |
| 7,055,730 B2 | 6/2006 | Ehrenfels et al. |
| 7,087,071 B2 | 8/2006 | Nicholas et al. |
| 7,121,446 B2 | 10/2006 | Arad et al. |
| 7,128,253 B2 | 10/2006 | Mastri et al. |
| 7,140,527 B2 | 11/2006 | Ehrenfels et al. |
| 7,159,750 B2 | 1/2007 | Racenet et al. |
| 7,188,758 B2 | 3/2007 | Viola et al. |
| 7,225,964 B2 | 6/2007 | Mastri et al. |
| 7,238,195 B2 | 7/2007 | Viola |
| 7,258,262 B2 | 8/2007 | Mastri et al. |
| 7,278,562 B2 | 10/2007 | Mastri et al. |
| 7,293,685 B2 | 11/2007 | Ehrenfels et al. |
| 7,296,722 B2 | 11/2007 | Ivanko |
| 7,308,998 B2 | 12/2007 | Mastri et al. |
| 7,326,232 B2 | 2/2008 | Viola et al. |
| 7,328,829 B2 | 2/2008 | Arad et al. |
| 7,334,717 B2 | 2/2008 | Rethy et al. |
| 7,398,907 B2 | 7/2008 | Racenet et al. |
| RE40,514 E | 9/2008 | Mastri et al. |
| 7,419,081 B2 | 9/2008 | Ehrenfels et al. |
| 7,424,965 B2 | 9/2008 | Racenet et al. |
| 7,434,716 B2 | 10/2008 | Viola |
| 7,458,494 B2 | 12/2008 | Matsutani et al. |
| 2004/0020963 A1 | 2/2004 | Sesek et al. |
| 2010/0176179 A1 | 7/2010 | Aoki |

TWO PIECE ANVIL FOR SURGICAL STAPLER

CROSS-REFERENCE TO RELATED APPLICATIONS

This application is a divisional of application Ser. No. 12/189,939, filed Aug. 12, 2008 now U.S. Pat. No. 7,942,304 which claims the benefit of and priority to U.S. Provisional Patent Application Ser. No. 60/981,129, filed on Oct. 19, 2007, the entire disclosure of which is incorporated by reference herein.

BACKGROUND

1. Technical Field

The present disclosure relates to surgical stapling apparatus, and more particularly, relates to a surgical stapler having a two piece anvil for deforming a staple.

2. Background of Related Art

Surgical staplers and other such devices for applying a staple to tissue are known in the art. Conventional stapling devices may be configured for use externally, i.e. wound closure, for use in open procedures, or for use in closed procedures, i.e. endoscopic or laparoscopic. When a surgical stapler is being used to join tissue, whether it be for wound closure or in an anastomotic procedure, the two portions of tissue must be approximated towards one another prior to stapling to ensure that each portion of tissue is pierced by at least one leg of the staple. Approximating the tissue portions towards one another requires manipulation of the tissue prior to stapling. Manipulating the tissue prior to stapling requires some degree of traction on the tissue and may require a free hand or additional instruments to accomplish. This problem is magnified during endoscopic and laparoscopic procedures where space is limited and access is minimal.

SUMMARY

A surgical stapling assembly for applying staples is disclosed. The stapling assembly includes a staple cartridge for retaining and selectively releasing a plurality of staples, a forming member engageable by a staple during formation thereof, and first and second anvil sections for forming the staples, wherein the first and second anvil sections are configured for independent actuation.

In a preferred embodiment, the forming member comprises a forming bar mounted to a distal portion of the staple cartridge, and the anvil sections from the staples around the forming bar. In a preferred embodiment, the anvil sections are operably mounted on the staple cartridge between the forming bar and the staple cartridge and actuation of the first anvil section deforms a first leg of a staple and actuation of the second anvil section deforms a second leg of a staple.

In a preferred embodiment, each of the staples in the staple cartridge has a backspan and first and second legs extending from the backspan, and the deforming leg of the first anvil section initially deforms the first leg of the staple and the deforming leg of the second anvil section subsequently deforms the second leg of the staple.

Further disclosed is a method of stapling tissue. The method of stapling includes the steps of providing a surgical stapler including a staple assembly having first and second anvil sections, positioning the surgical stapler near a first flap of tissue to be stapled, actuating the staple assembly such that first anvil section deforms a first leg of a staple, approximating the first tissue flap towards a second tissue flap, and further actuating the staple assembly, thereby causing the second anvil section to deform a second leg of the staple. The method may further include the step of releasing the actuation member, thereby disengaging first and second anvil section from about the staple.

A method of stapling first and second sections of tissue is also disclosed wherein the method comprises the steps of:

providing a surgical stapler including at least one staple having first and second legs and first and second anvil sections;

positioning the surgical stapler near the first portion of tissue to be stapled;

advancing the first anvil section to deform the first leg of a staple;

approximating the first tissue section towards the second tissue section; and subsequently advancing the second anvil section to deform the second leg of the staple.

Preferably, advancing the first anvil section deforms the first staple leg to extend inwardly toward the second staple leg and advancing the second anvil section deforms the second staple leg to extend inwardly toward the first staple leg to form a substantially box-shaped staple.

In one embodiment, the step of subsequently advancing the second anvil section comprises the step of fully actuating an actuator after partial actuation to advance the first anvil section. In another embodiment, the step of subsequently advancing the second anvil section comprises the step of actuating a second actuator after actuation of a first actuator to advance the first anvil section.

BRIEF DESCRIPTION OF THE DRAWINGS

The foregoing summary, as well as the following detailed description will be better understood when read in conjunction with the appended figures. It is understood, however, that the present disclosure is not limited to the precise arrangement and instrumentalities shown.

DETAILED DESCRIPTION OF THE EMBODIMENTS

Figure 1:
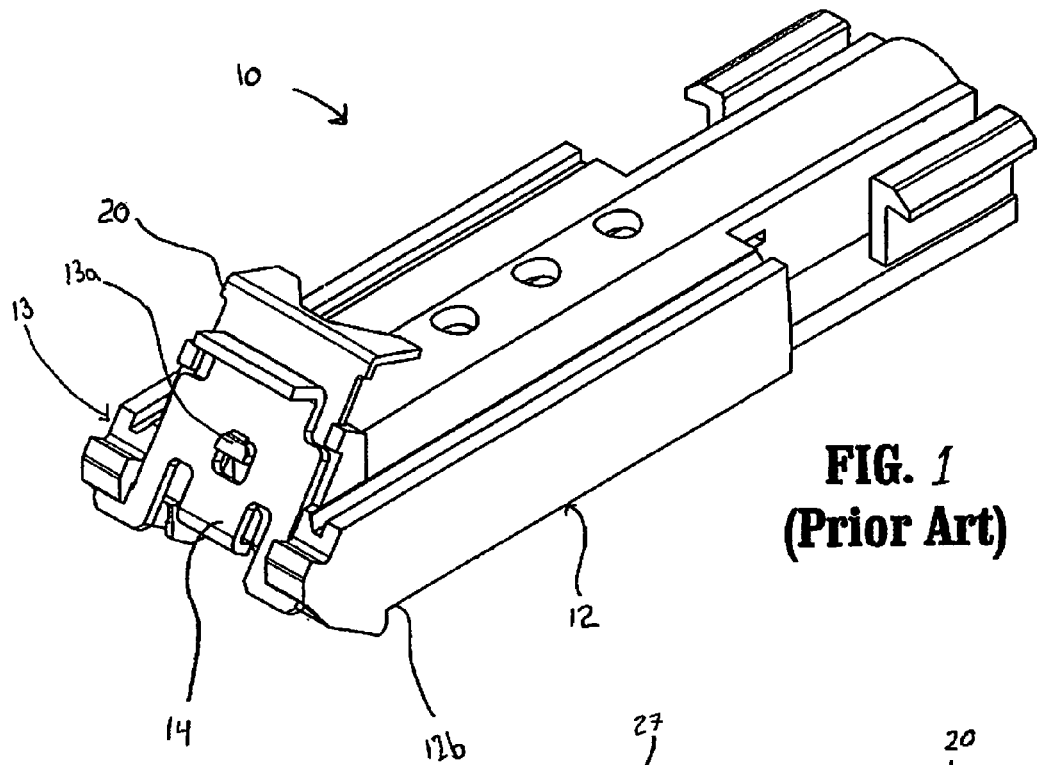
FIG. 1 is a perspective view of a prior art stapling assembly.

Reference will now be made to the drawings wherein like reference numerals illustrate similar components throughout the several views. As shown in the drawings and as described throughout the following description, as is traditional when referring to relative positioning of an object, the term "proximal" refers to the end of the apparatus which is closer to the user and the term "distal" refers to the end of the apparatus which is further from the user.

Referring initially to FIGS. 1-4, a prior art staple assembly is shown generally as staple assembly 10. Briefly, staple assembly 10 includes a staple cartridge 12 including a mounting assembly 13 on a distal end 12b thereof, a forming bar 14 mounted on a tab 13a formed on mounting assembly 13, and a one piece anvil 20 slidably mounted on tab 13a of mounting assembly 13 between forming bar 14 and distal end 12b of cartridge 12. Cartridge 12 is configured to retain a plurality of staples (not shown). Staple assembly 10 is further configured to deform and release a staple 50 (FIG. 3) upon actuation thereof. For purposes of the following disclosure, prior to deformation (FIG. 3), staple 50 is a generally U-shaped member having a backspan 52 and parallel first and second legs 52a, 52b extending therefrom. Once deformed, staple 50 defines a substantial box shape (FIG. 4) wherein first and second legs 52a, 52b are moved towards one another. The actuation of stapling assembly 10 is described in commonly assigned U.S. Pat. Nos. 5,289,963 and 5,560,532, the entire contents of each are hereby incorporated by reference, and will not be discussed in further detail herein.

Figure 2:
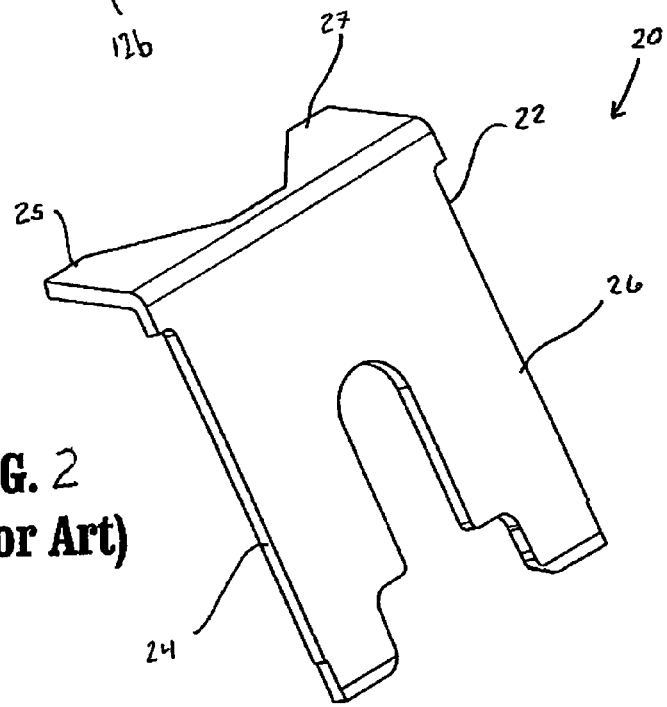
FIG. 2 is a perspective view of a prior art anvil for use in the stapling assembly of FIG. 1.
Figure 3:
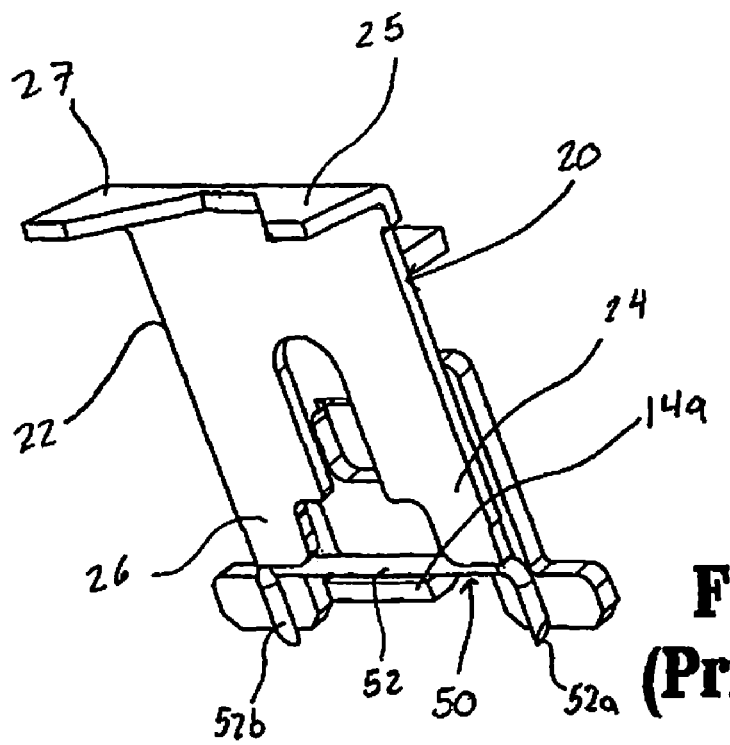
FIG. 3 is perspective rear view of the distal end of the prior art stapling assembly of FIG. 1 in a first position.
Figure 4:
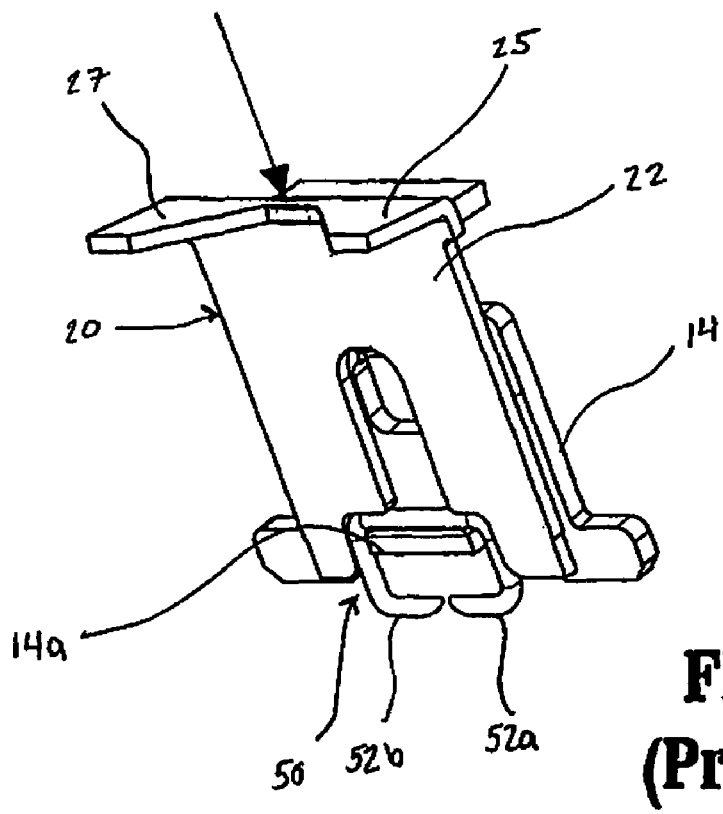
FIG. 4 is a rear view of the distal end of the prior art stapling assembly of FIG. 1 in a second position.

With particular reference to FIGS. 2 and 3, prior art one piece anvil 20 includes a base 22, a pair of forming legs 24, 26 for deforming staple 50 and a corresponding pair of prongs 25, 27 for engaging an actuation member. Turning now to FIGS. 3 and 4, forming bar 14 includes a forming member 14a. Forming member 14a is substantially parallel to the staple backspan 52 and is configured to retain staple 50 as forming legs 24, 26 of anvil 20 deform staple 50 thereabout.

Staple assembly 10 operates to deform staple 50 so as to pinch or retain a first and second flap of tissue $T_1$, $T_2$ (FIG. 14) between first and second legs 52a, 52b of staple 50. Operation of staple assembly 10 requires that the first and second flaps of tissue be approximated towards one another prior to stapling. As discussed above, manipulation of either or both flaps of tissue requires some degree of traction on the tissue. This additional manipulation of the tissue to approximate the flaps sufficiently so that they may be stapled together using a device having a one piece anvil may not be possible, depending on the location of the target site and the condition of the surrounding tissue. This is especially true for endoscopic or laparoscopic procedures where space is limited and access is minimal.

Referring now to FIGS. 5-14, a staple assembly 110 of the present disclosure including a two piece anvil 120 is shown. Staple assembly 110 is substantially similar to staple assembly 10 in some respect and will only be described in relation to the differences therebetween.

Figure 5:
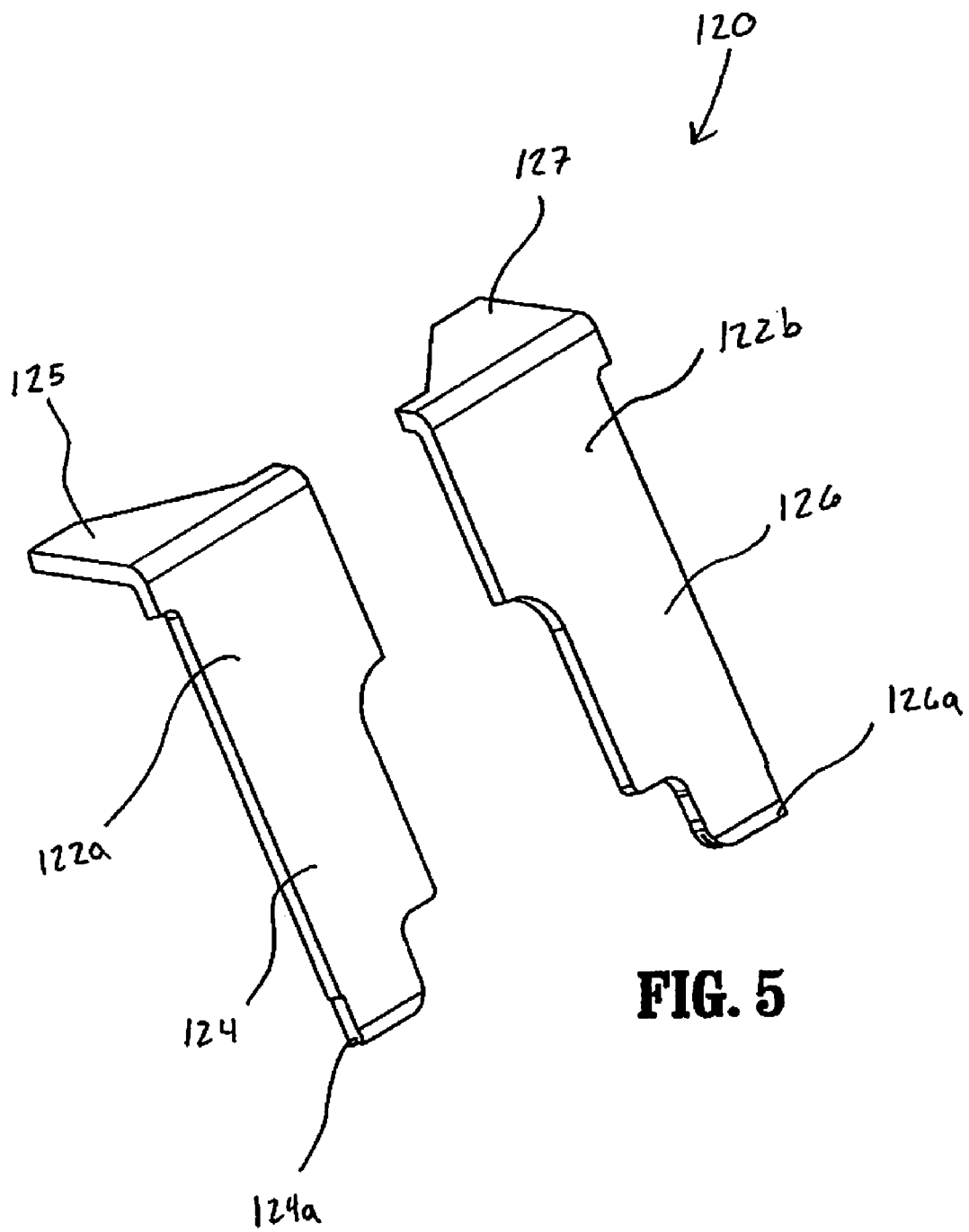
FIG. 5 is a perspective view of a two piece anvil according to the present disclosure.

Referring initially to FIG. 5, two piece anvil 120 includes first and second anvil sections 122a, 122b slidable relative to each other. First and second anvil sections 122a, 122b are substantial mirror images of one another. Each of first and second anvil sections 122a, 122b includes a forming leg 124, 126 and an engagement prong 125, 127, respectively. Distal end 124a, 126a of forming legs 124, 126, respectively, may define a lip or groove for more securely engaging base 52 of staple 50 (FIG. 6) during actuation of staple assembly 110. As will be discussed in greater detail below, first and second anvil sections 122a, 122b are configured to he actuated independently of one another.

Figure 6:
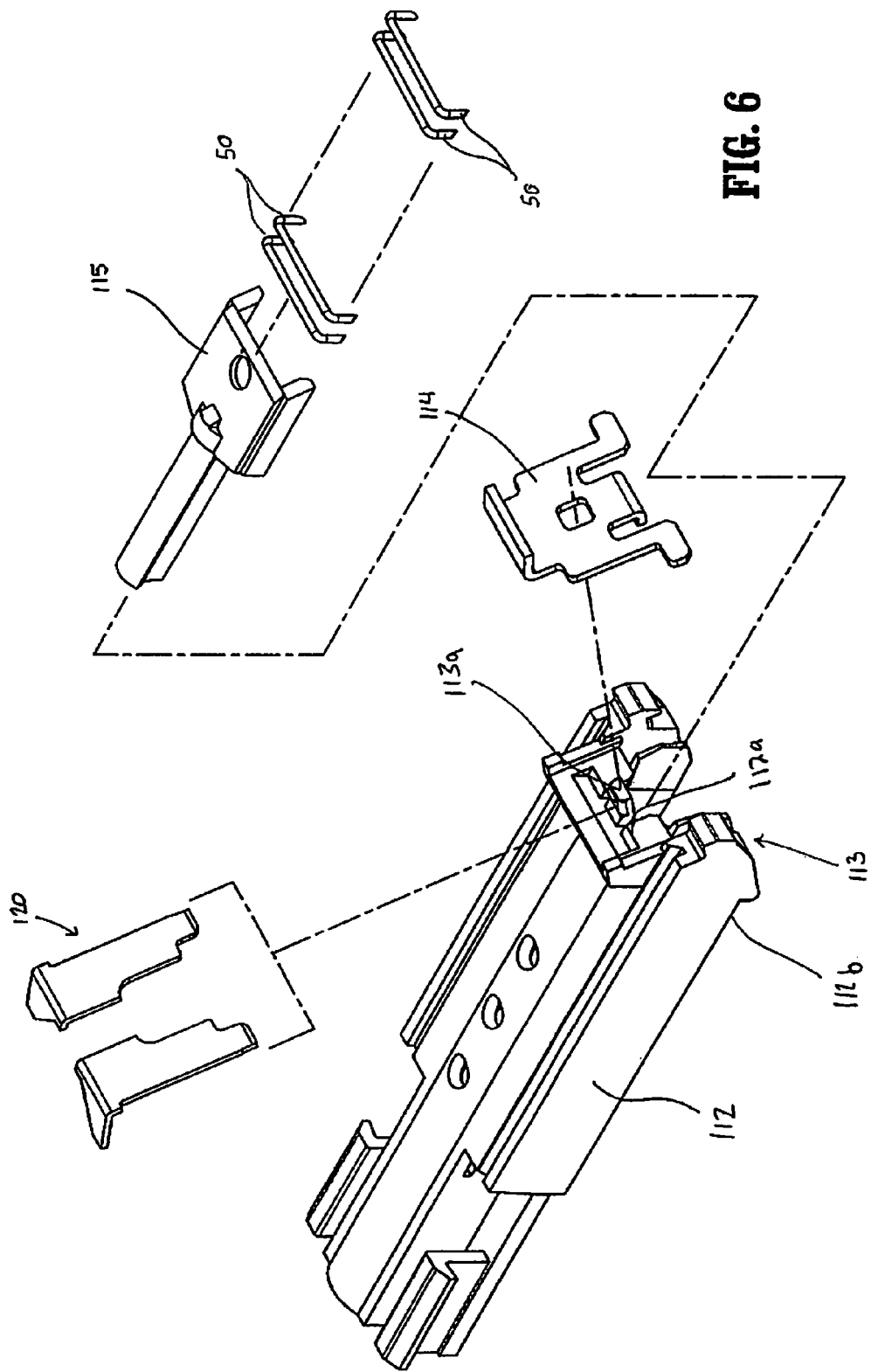
FIG. 6 is an exploded view of a stapling assembly including the two piece anvil of FIG. 5.

Turning briefly to FIG. 6, staple assembly 110 includes a mounting assembly 113 on a distal end 112b of cartridge assembly 112. Mounting assembly 113 includes a tab 113a. Two piece anvil 120 is slidably mounted on a tab 113a between forming member (bar) 114 and distal end 112a of cartridge assembly 112, with the tab 113a extending through the opening in the forming bar 114. A staple pusher 115 biases staples 50 towards forming surface 114a of forming bar 114.

Figure 7:
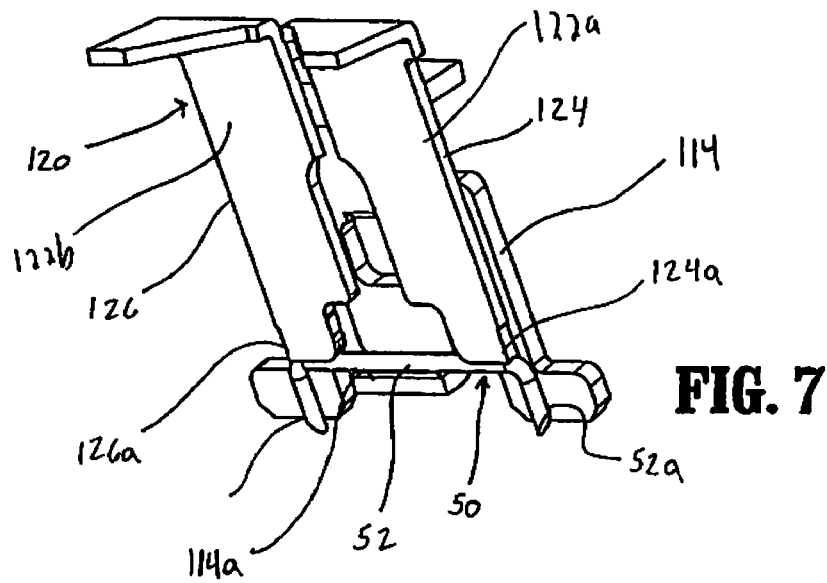
FIG. 7 is a rear view of the distal end of the stapling assembly of FIG. 6 in a first position.
Figure 8:
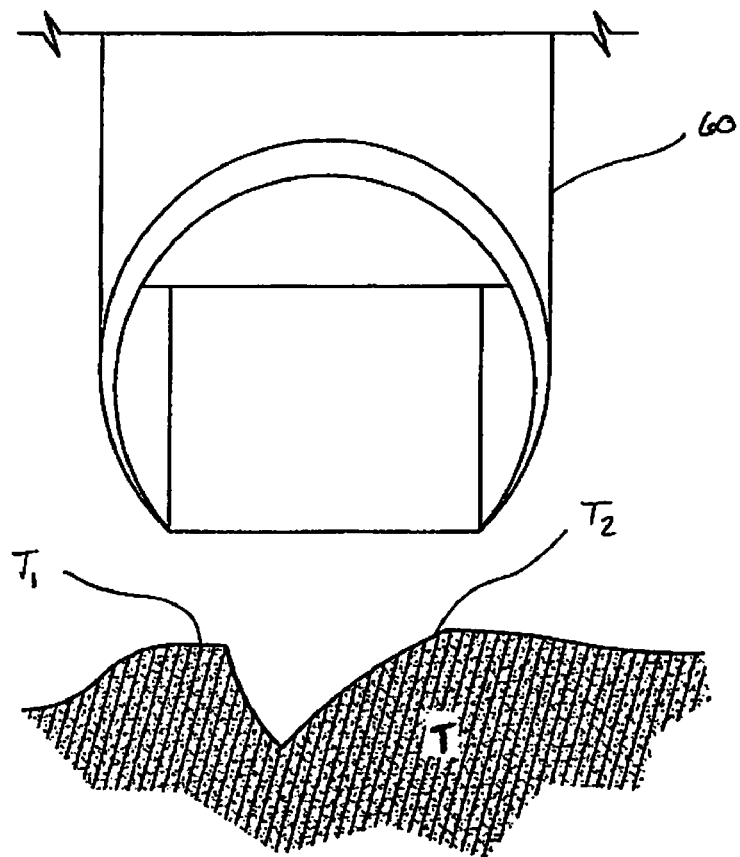
FIG. 8 is an end view of the surgical stapling device prior to stapling tissue.
Figure 9:
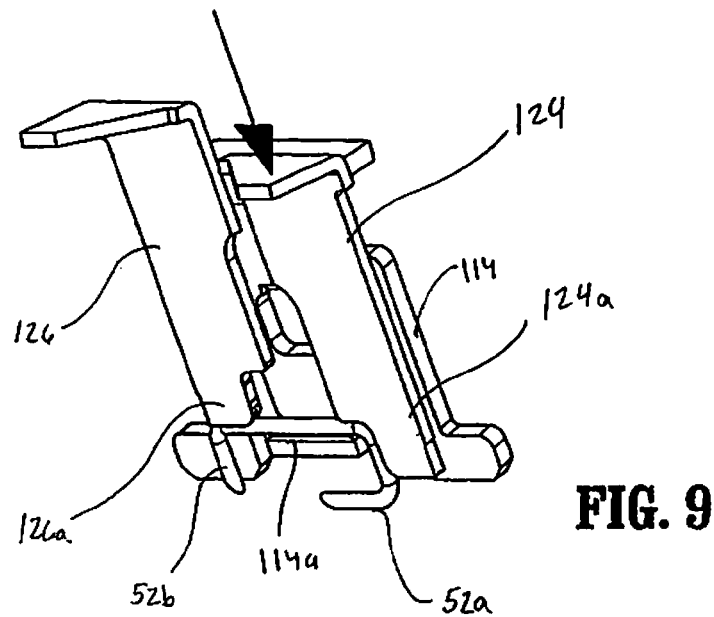
FIG. 9 is a rear view of the distal end of the stapling assembly of FIG. 6 in a second, partially actuated position.
Figure 10:
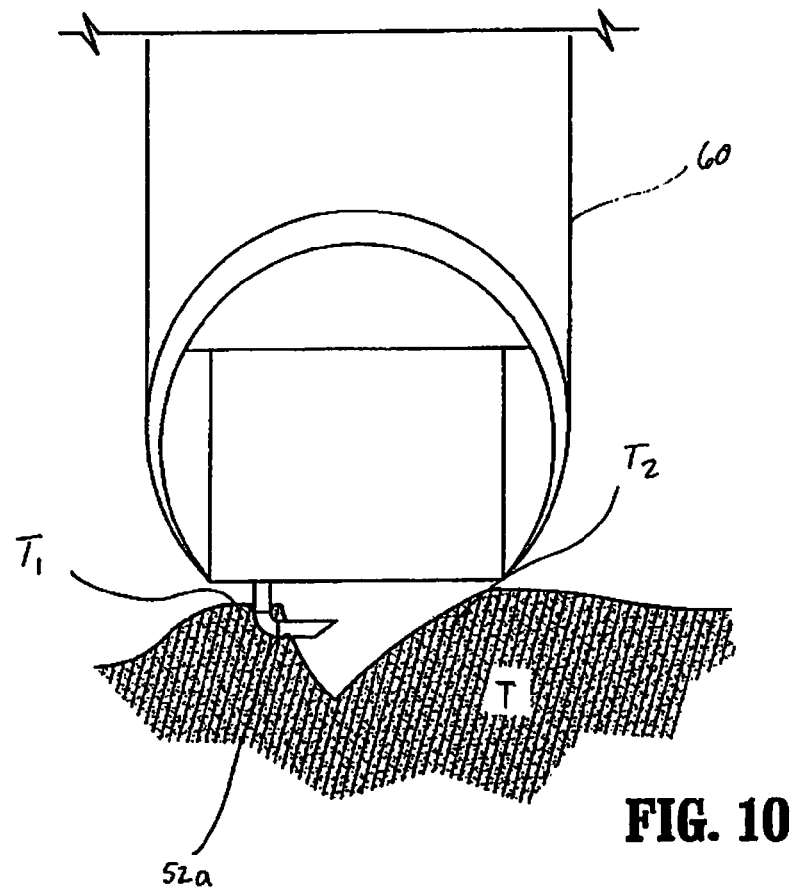
FIG. 10 is an end view of the surgical stapling device of FIG. 8 in a partially actuated position.
Figure 11:
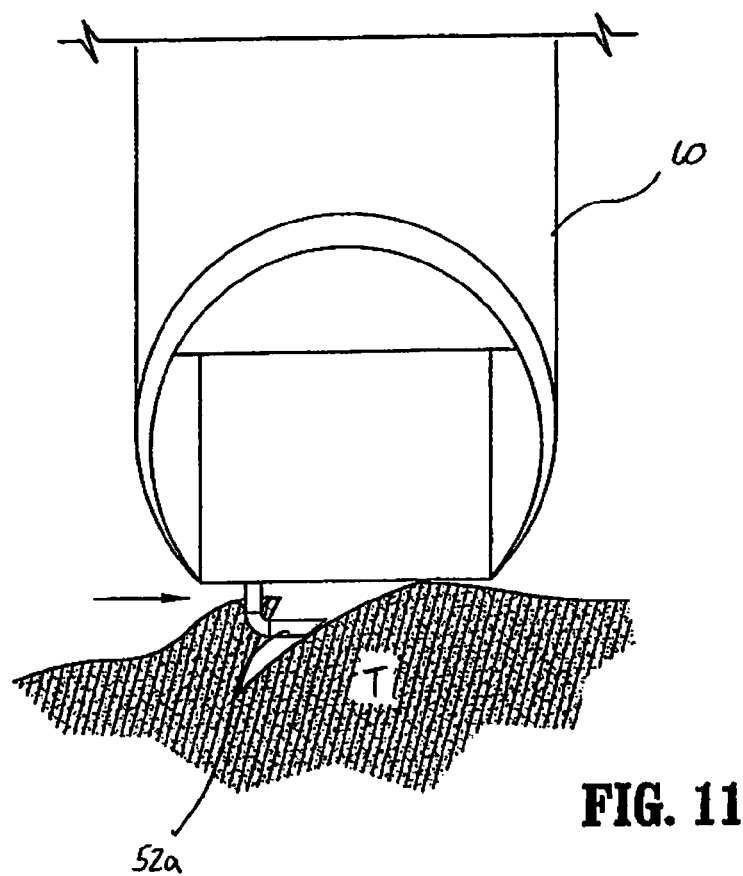
FIG. 11 is an end view of the surgical stapling device of FIG. 8 showing approximation of the tissue sections.

The operation of staple assembly 110 will now be described with reference to FIGS. 7-14. Initially, staple 50 is positioned between forming member 114a of forming bar 114 and distal ends 124a, 126a of forming legs 124, 126 of two piece anvil 120 (FIG. 7). The distal end 60 of a surgical stapling device (not shown) is approximated near a first flap of tissue $T_1$ to be stapled. Partial actuation of an actuation mechanism (not shown) causes first anvil section 122a of two piece anvil 120 to advance towards forming member 114a, thereby deforming first leg 52a of staple 50 about forming bar 114 and piercing first flap of tissue $T_1$ (FIG. 10). The piercing of first flap of tissue $T_1$ with first leg 52a of staple 50 permits a surgeon to approximate first flap of tissue $T_1$ towards second flap of tissue $T_2$.

Figure 12:
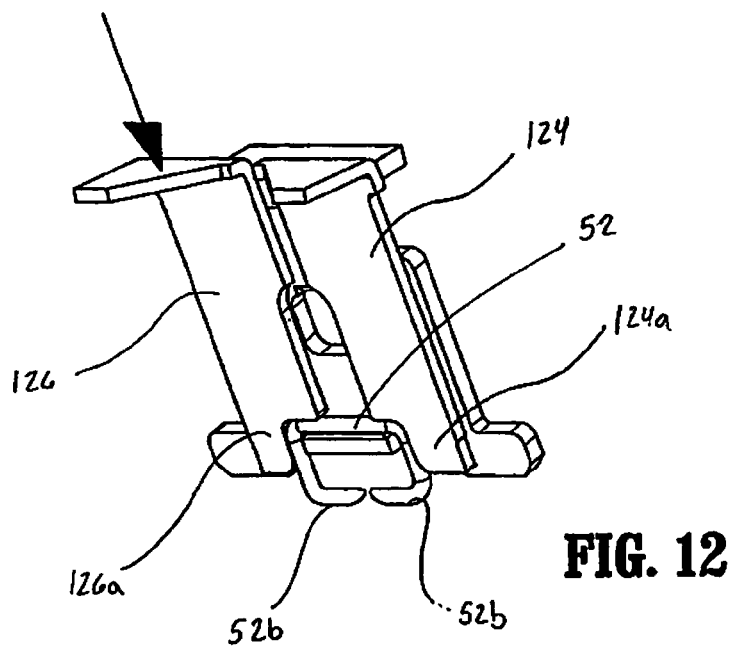
FIG. 12 is a rear view of the distal end of the stapling assembly of FIG. 6 in a completely actuated position.
Figure 13:
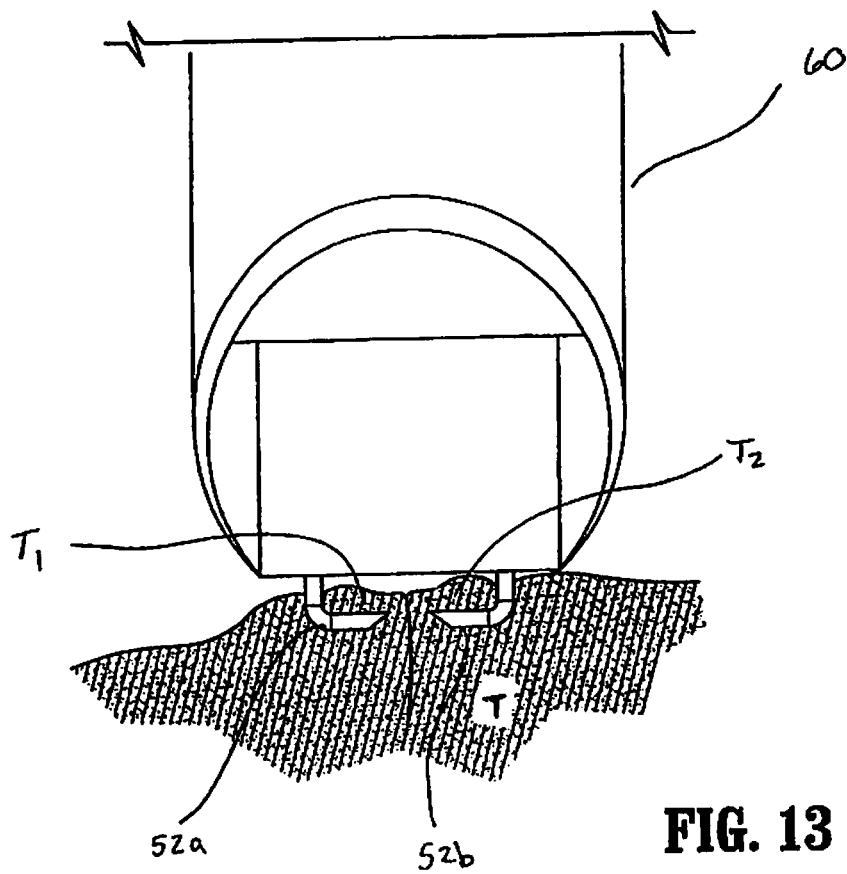
FIG. 13 is an end view of the surgical stapling device of FIG. 8 in a completely actuated position.
Figure 14:
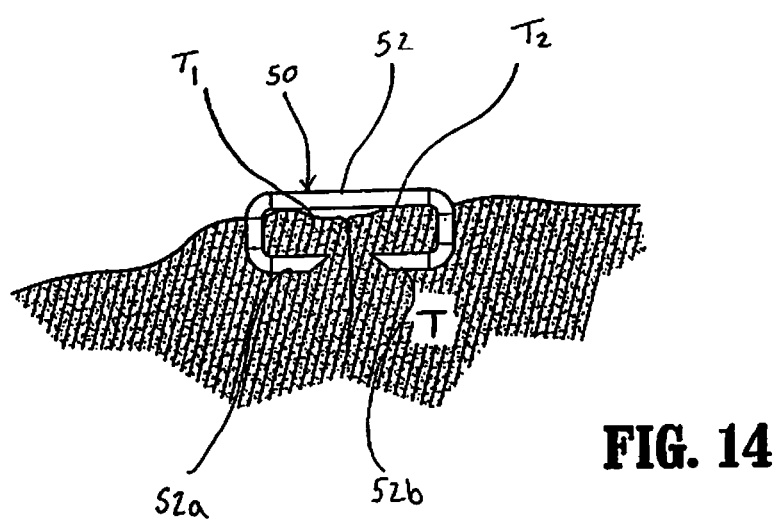
FIG. 14 is a cutaway view of a deformed surgical staple retaining two portions of tissue.

Once first and second flaps of tissue $T_1$, $T_2$ are sufficiently approximated towards one another (FIG. 11) the stapling thereof may be completed. Further actuation of actuation mechanism (not shown) causes second anvil section 126 of two piece anvil 120 to advance towards forming bar 114, thereby deforming second leg 52b of staple 50 about forming bar 114 (FIG. 12). In this manner, second leg 52b of staple 50 pierces second tissue flap $T_2$, thereby retaining first and second tissue flaps $T_1$, $T_2$ in an approximated relationship with one another (FIG. 13). Release of the actuation mechanism (not shown) causes the retraction of two piece anvil 120, thereby releasing deformed staple 50 from stapling assembly 110 (FIG. 14).

Unlike with prior art staplers, during wound closure procedures using a surgical stapler incorporating a two piece anvil 120, first and second flaps of tissue $T_1$, $T_2$ do not need to be manipulated prior to stapling. Thus, traction on either the first and/or second flap of tissue $T_1$, $T_2$ prior to stapling is unnecessary to effect proper closure. In this manner, a surgeon need not need touch tissue T prior to stapling, nor docs the surgeon need a free hand or second device to approximate the first and second flaps of tissue $T_1$, $T_2$ towards one another. It is envisioned that the aspects of the present disclosure may be adapted for staples having any number of sizes and configurations.

As described above, independent actuation of the anvil sections occurs as the actuator upon partial advancement advances the first anvil section and upon further advancement (e.g. full actuation) advances the second anvil section. However, alternatively, a separate actuator could be utilized to advance each of the anvil sections which can occur in sequential steps, e.g. the second actuator can be actuated after full or partial actuation of the first actuator.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure.

What is claimed is:

1. A method of stapling tissue, the method comprising the steps of:
    providing a surgical stapler including a staple assembly, a first anvil section and a second anvil section;
    positioning the surgical stapler near a first flap of tissue to be stapled;
    actuating the staple assembly such that first anvil section deforms a first leg of a staple while a second staple leg is not deformed;
    approximating the first tissue flap towards a second tissue flap; and
    further actuating the staple assembly, thereby causing the second anvil section to deform a second leg of the staple subsequent to deformation of the first leg of the staple.

2. A method of stapling tissue according to claim 1, further including the step of releasing the actuation member, thereby disengaging first and second anvil sections from about the staple.

3. A method of stapling tissue according to claim 1, wherein the step of further actuating the stapling assembly comprises the step of fully actuating an actuator after partial actuation to advance the first anvil section.

4. A method of stapling tissue according to claim 1, wherein the step of actuating the stapling assembly such that the first anvil section deforms a first leg of a staple includes the step of advancing longitudinally the first anvil section.

5. A method of stapling tissue according to claim 4, wherein the step of further actuating the stapling assembly to cause the second anvil section to deform a second leg of a staple includes the step of advancing longitudinally the second anvil section.

6. A method of stapling tissue according to claim 5, wherein the first and second anvil sections engage the backspan of the staple.

7. A method of stapling tissue according to claim 1, wherein the step of further actuating the stapling assembly to cause the second anvil section to deform a second leg of a staple includes the step of advancing longitudinally the second anvil section.

8. A method of stapling tissue according to claim 1, wherein the first and second anvil sections engage the backspan of the staple.

9. A method of stapling tissue according to claim 1, wherein the first anvil section is movable in a distal direction and the second anvil section is movable in a distal direction independent of distal movement of the first anvil section.

10. A method of stapling tissue according to claim 1, wherein the first and second anvil sections have forming legs with distal ends and the first and second anvil sections are advanceable to form the staple around a forming bar, the staple initially positioned between the forming bar and the distal end of the forming legs.

11. A method of stapling first and second sections of tissue, the method comprising the steps of:
    providing a surgical stapler including at least one staple having first and second legs extending from a backspan and a first anvil section and a second anvil section;
    positioning the surgical stapler near the first portion of tissue to be stapled;
    advancing the first anvil section to deform the first leg of a staple;
    approximating the first tissue section towards the second tissue section; and
    subsequently advancing the second anvil section independent of advancement of the first anvil section to deform the second leg of the staple after deformation of the first leg of the staple.

12. A method of stapling tissue according to claim 11, wherein advancing the first anvil section deforms the first staple leg to extend inwardly toward the second staple leg and advancing the second anvil section deforms the second staple leg to extend inwardly toward the first staple leg to form a substantially box-shaped staple.

13. A method of stapling tissue according to claim 12, wherein the step of subsequently advancing the second anvil section comprises the step of fully actuating an actuator after partial actuation to advance the first anvil section.

14. A method of stapling tissue according to claim 11, wherein the step of subsequently advancing the second anvil section comprises the step of actuating a second actuator after actuation of a first actuator to advance the first anvil section.

15. A method of stapling tissue according to claim 1, wherein the steps of advancing the first anvil section and advancing the second anvil section include the steps of engaging a backspan of the staple and advancing the staple into engagement with a staple forming member.

16. A method of stapling tissue according to claim 1, wherein the first and second anvil sections have forming legs with distal ends and the anvil sections are advanceable to form the staple around a forming bar, the staple initially positioned between the forming bar and the distal end of the forming legs.

17. A method of stapling tissue according to claim 11, wherein the first and second anvil sections are advanced longitudinally distally.

* * * * *